United States Patent [19]
Lancaster et al.

[11] Patent Number: 5,311,880
[45] Date of Patent: May 17, 1994

[54] METHOD AND APPARATUS FOR OBJECTIVE EVALUATION OF PATIENT AMBULATION, BALANCE AND WEIGHT BEARING STATUS

[76] Inventors: Eric B. Lancaster, 311 E. Sycamore, Independence, Kans. 67301; Michael F. Kocher, 7363 Yosemite, Lincoln, Nebr. 68507

[21] Appl. No.: 47,092

[22] Filed: Apr. 14, 1993

[51] Int. Cl.$^5$ .............................................. A61B 5/103
[52] U.S. Cl. .................................... 128/782; 482/68; 135/67
[58] Field of Search .................. 128/774, 782; 135/67, 135/82, 85; 482/66, 68

[56] References Cited

U.S. PATENT DOCUMENTS

| | | | |
|---|---|---|---|
| 3,690,652 | 9/1972 | Schneider | 482/66 |
| 4,384,713 | 5/1983 | Deutsch et al. | 482/68 |
| 4,621,804 | 11/1986 | Mueller | 135/67 |
| 4,765,355 | 8/1988 | Kent | 135/67 |
| 4,869,279 | 9/1989 | Hedges | 482/66 |
| 5,167,597 | 12/1992 | David | 482/68 |

OTHER PUBLICATIONS

Zhenxing Jin, BS and Howard Jay Chizeck, ScD, *Instrumented parallel bars for three-dimensional force measurement*, 1992, pp. 31–38.
Thomas Pillar, MD; Ruth Dickstein, DSc; Zvi Smolinski, MSc, *Walking reeducation with partial relief of body weight in rehabilitation of patients with locomotor disabilities*, 1991, pp. 47–52.
Robert L. Waters, MD; Joy S. Yakura, MS, PT; Rodney Adkins, PhD; Greg Barnes, BS, PT, *Determinants of Gait Performance Following Spinal Cord Injury*, Nov., 1989, pp. 811–818.
Eng H. Lee, MD, James C. H. Goh, PhD, Kamal Bose, MBBS, *Value of Gait Analysis in the Assessment of Surgery in Cerebral Palsy*, Jul., 1992, pp. 642–646.
David E. Krebs, Joan Edelstein, and Sidney Fishman, *Reliability of Observational Kinematic Gait Analysis*, Jul., 1985, pp. 1027–1033.
Lois Finch, Hugues Barbeau, Bertrand Arsenault, *Influence of Body Weight Support on Normal Human Gait: Development of a Gait Retraining Strategy*, Nov., 1991, pp. 842–856.
Elizabeth Dean, PhD, Jocelyn Ross, BSR, Joan Bartz, PT, Susan Purves, PT, *Improving the Validity of Clinical Exercise Testing: The Relationship Between Practice and Performance*, Aug., 1969, pp. 599–604.
Shan P. Tsai, PhD, Elizabeth L. Gilstrap, MS, Sally R. Cowles, MD, DrPH, Louis C. Waddell, Jr., MD, Charles E. Ross, DO, MS, *Personal and Job Characteristics of Musculoskeletal Injuries in an Industrial Population*, Jun., 1992, pp. 606–612.
Christopher J. Hughes, PhD, Wendi H. Weimar, MS, Pradip N. Sheth, PhD, Clifford E. Brubaker, PhD, *Biomechanics of Wheelchair Propulsion as a Function of Seat Position and User-to-Chair Interface*, Mar., 1992, pp. 263–269.
R. Lee Kirby, MD, Susan M. Atkinson, BSc (Hon), Elizabeth A. MacKay, BSc (Hon), *Static and Dynamic Forward Stability of Occupied Wheelchairs: Influence of Elevated Footrests and Forward Stabilizers*, Sep., 1989, pp. 681–686.
David L. Wright, Tammy L. Kemp, *The Dual-Task Methodology and Assessing the Attentional Demands of Ambulation with Walking Devices*, Apr., 1992, pp. 306–315.
Sally A. Rose, Sylvia Ounpuu, Peter A. DeLuca, *Strategies for the Assessment of Pediatric Gait in the Clinical Setting*, Dec., 1991, pp. 961–980.
Deborah L. Wilkerson, Ma, Andrew I. Batavia, JD, Gerben DeJong, PhD, *Use of Functional Status Measures for Payment of Medical Rehabilitation Services*, Feb., 1992, pp. 111–120.

*Primary Examiner*—Max Hindenburg
*Attorney, Agent, or Firm*—Richard P. Stitt

[57] ABSTRACT

A walker is provided which is equipped with detectors for measuring various loads and torques placed thereon by a user including right side and left side loads as well as torque loads on the handles of the walker and having time and distance detectors to allow the ambulation status of a user to be progressively monitored by medical personnel.

19 Claims, 1 Drawing Sheet

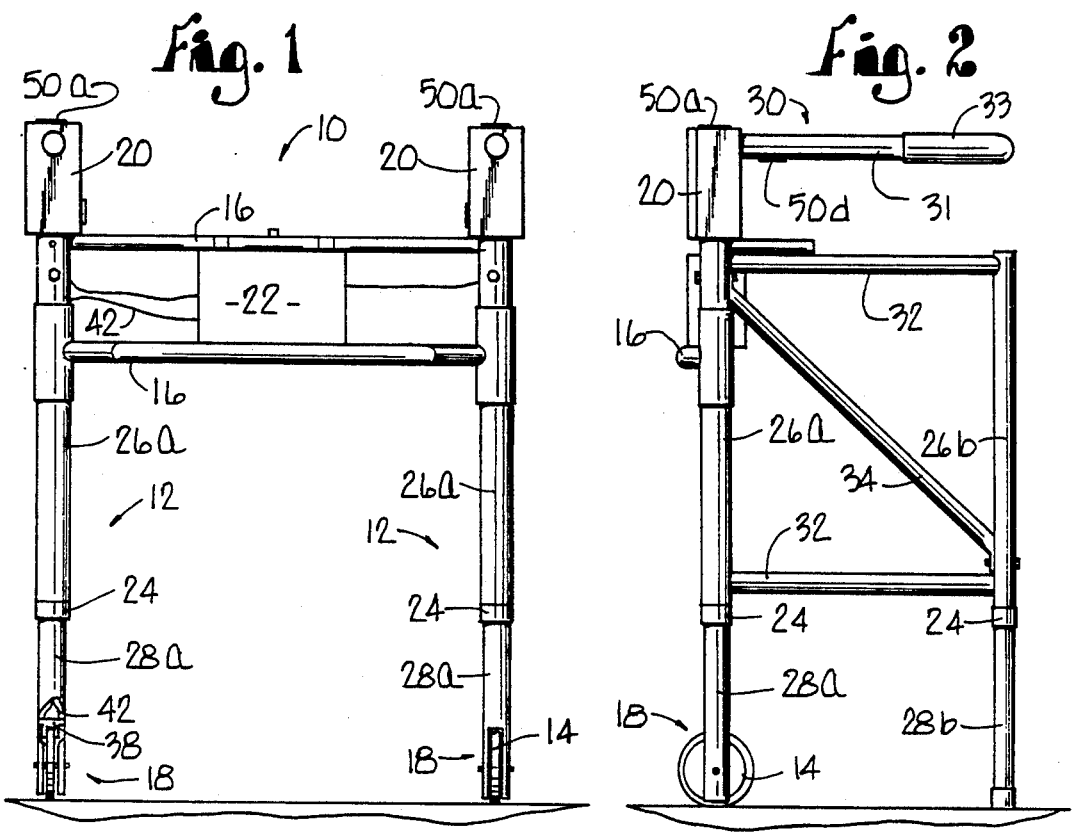
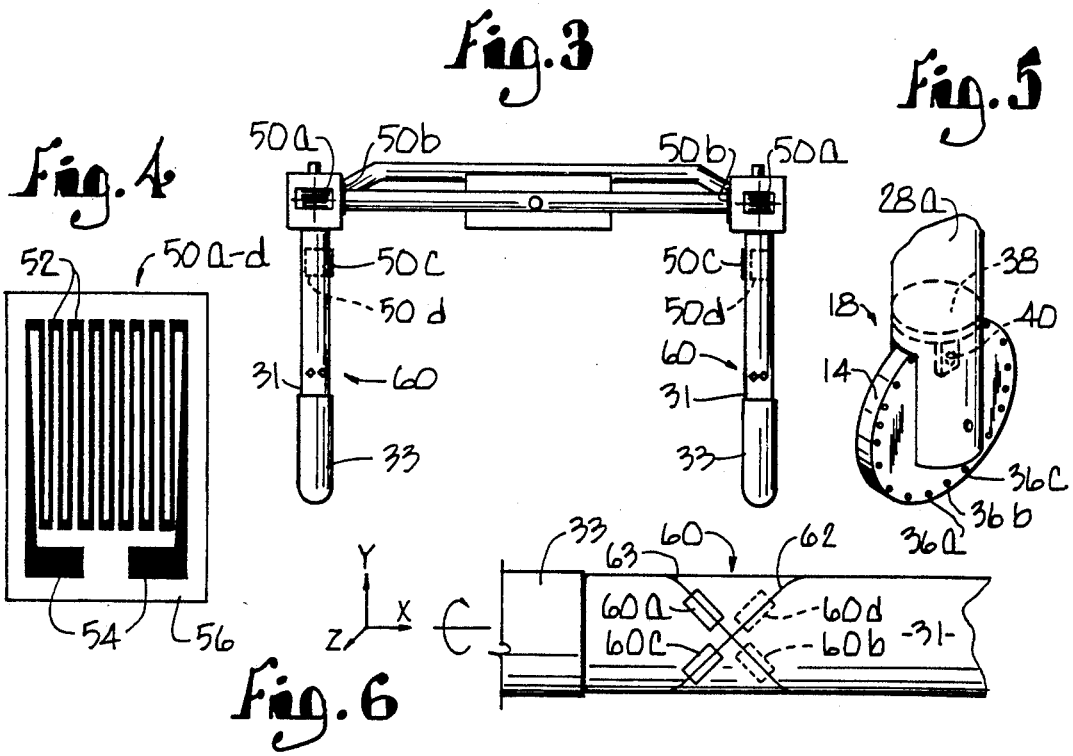

METHOD AND APPARATUS FOR OBJECTIVE EVALUATION OF PATIENT AMBULATION, BALANCE AND WEIGHT BEARING STATUS

BACKGROUND OF THE INVENTION

In any injury affecting ambulation, balance, or general physical mobility of a patient it is the goal of physical therapy, and medicine in general, to contribute therapy and treatment to the patient in order to restore these abilities to the highest possible level with respect to the circumstances of age of the patient and the degree of injury sustained. This goal dictates a requirement for assessment of patient improvement during the course of therapy. Such assessment of patient improvement is necessary for both evaluation of the quality and kind of therapy as well as for justification to physicians and insurance providers of continuation of the course of therapy.

The ability to measure and document significant improvement in a patient versus de minimis changes in patient physical ability increasingly is becoming necessary for continuation of treatment protocols. In addition, the ability to objectively measure the various aspects of a patient's physical abilities during a course of treatment or healing of an injury can be utilized to detect patient adherence to the recommendations of the physical therapist or physician. Typically, when out of view of treating medical personnel, it is common for patients to neglect recommended therapies such as prescribed exercises or premature use of a healing limb. This can lead to delay in healing as well as further injury. Yet another area where objective data is useful is in the evaluation of work related injuries for determination of the degree of debilitation of the worker and consequently the evaluation of compensation due the worker.

Heretofore, evaluation of a patient during the term of treatment or analysis of patient debilitation largely has been unquantified. Subjective criteria for determination of patient status have been used by therapists and physicians. Typically, the patient will be observed during the course of a series of movements, and the general impressions of the evaluator will be noted and compared over time. Such observational evaluation can be skewed by many different factors such as patient adherence to treatment protocols, patient desire to be deemed fit for work, therapist desire for monetary gain from continued treatment, and even the personal relationship between patient and therapist.

Therefore, an objective method and apparatus for making quantifiable determinations of patient improvement is needed. Such a method and apparatus should permit collection of reproducible, objective data on patient ambulation, balance, and weight bearing status as well as proprioception in injured areas. The ability to objectively document patient status and improvement over a course of therapy can provide valuable information to the patient, the physician and therapist, and improvement in patient therapy by enabling concise communication between physician and therapist and identification of areas of patient progress versus injuries not responding to treatment.

The availability of objective measurements and data can permit development of consistent medical standards for use in determining whether patient improvement is small, but significant, indicating continuation of treatment, or insignificant indicating the treatment should be changed or discontinued. The availability of objective measurements and data can also be used to develop consistent medical standards for normal functionality and levels of functionality/disability. Such standards of medical evaluation can assist in allocation of medical resources to treatments of greatest utility and to those patients exhibiting more than marginal benefit from treatment.

Therefore it is an object of the present invention to provide an apparatus capable of providing objective quantification of patient ambulation and the balance and weight bearing status during ambulation as well as to provide indication of proprioception status of injured areas;

Another object of the invention is to provide documentation of patient response to therapy for evaluation by physicians and physical therapists;

An object of the present invention is to provide a source of objective feedback to a patient as a means of demonstrating patient success in a course of therapy and to encourage the patient to sustain the course of therapy;

Yet another object of the present invention is to provide a means of evaluating marginally successful treatments versus treatments providing substantial benefits for a patient;

Also, another object of the present invention is to provide a means of specific identification of patient difficulties during ambulation;

Another object of the present invention is to allow therapists and physicians to determine areas of patient improvement with respect to an injury versus aspects of the injury which are unresponsive to the course of treatment;

Yet another object of the present invention is to allow collection of objective data in order to establish and evaluate short term and long term goals with respect to a course of therapy;

Still another object of the present invention is to provide an objective measurement of patient adherence to therapy and to allow more accurate determination of appropriate patient discharge from therapy.

Other objects and advantages of this invention will become apparent from the following description taken in connection with the accompanying drawings, wherein is set forth by way of illustration and example, an embodiment of this invention.

SUMMARY OF THE INVENTION

The present invention provides an apparatus and method for collection and evaluation of data related to patient ambulation, patient balance, and weight bearing status through measurement of various weight loads and strains placed upon a walker-type structure during the course of patient activity.

Further, a method is provided for collecting data relating to patient ambulation, balance, weight bearing status and proprioception to permit evaluation of patient treatment, patient adherence to a treatment regimen, and treatment success.

The apparatus for performing the above data collection comprises a walker-type structure capable of being moved and assisting a user during the course of ambulation, the structure contains strain, stress, and force, including torque, measuring sensors at various locations in order to identify the type and amount and location of loads or strains or torques being placed upon the device by a user or patient during the course of ambulation. Determinations of patient status are accomplished by detecting the various user forces, including torques, applied to the apparatus due to the user relying on the device to support components of the user's weight during movement. This is followed by comparative evaluation of patient data.

The method and apparatus can also incorporate means for time and distance measurements such as an interval timer and a distance measuring wheel and a counter in order to determine rapidity of patient ambulation and speed of travel. The measurement of the various user forces and torques applied to the apparatus and utilized in the method of the invention may be measured either by strain gauge devices applied to the apparatus or by mechanical measurement of the forces and torques applied to the apparatus through spring compression-type or torsion-type devices. Additional, alternative and equivalent types of devices for measuring the forces and torques applied to the apparatus include link, beam, ring, and shear-web load cells, piezoresistive devices, and devices for measuring deflection of a beam.

In particular, and without limitation, a preferred embodiment of the apparatus incorporates resistance-wire strain detectors on the apparatus handle assemblies to measure the various strains on the handles resulting from the change in forces, including torques, applied to the handles from a user's reliance on the apparatus to bear the weight of the user during the course of ambulation.

The method for objective evaluation of patient ambulation, balance and weight bearing status and proprioception comprises the steps of: providing a user with a moveable frame apparatus for supporting user weight during ambulation, equipping the apparatus with load and torque measuring sensors to determine user reliance on the apparatus during ambulation by measurement of the application of forces and torques to the device from supporting the weight of a user by the device, measuring the forces and torques on the device during user ambulation, and evaluating the detected forces and torques on the device to determine patient physical status.

DESCRIPTION OF THE DRAWINGS

FIG. 1 is a front elevational view of the walker showing a data gathering unit mounted between the front lateral braces;

FIG. 2 is a left side elevational view of the walker of FIG. 1 showing the handle assembly extending from the leg assembly;

FIG. 3 is a top plan view of the walker, with the leg assembly structure removed for clarity and showing the placement of load measurement gauges thereon;

FIG. 4 is an enlarged plan view of a typical resistance wire strain or load gauge;

FIG. 5 is an enlarged fragmentary view of the base of the left front upright of FIG. 1 and showing in phantom lines the positioning of a detector therein; and FIG. 6 is a top plan enlarged fragmentary view of a handle of FIG. 3 showing the placement of the top torque gauges and in phantom lines the bottom torque gauges.

DESCRIPTION OF THE PREFERRED EMBODIMENT

Referring now to FIG. 1, walker 10 can be seen to be generally configured on the shape of conventional walkers currently in use. Walker 10 is composed of a light weight metal such as aluminum. Inventive walker 10, however, has been configured with a distance measuring device or distance gauge 18 located in the base of leg assembly 12. In this particular embodiment, distance gauge 18 is in the form of wheel 14 mounted in leg assembly 12. Walker 10 is provided with sufficient space between leg assemblies 12 to enable a user to stand between leg assemblies 12. Leg assemblies 12 are joined by lateral braces 16 which provide structural integrity to walker 10 and allow leg assemblies 12 to function as a unit. Located between lateral braces 16 is data console 22 which serves as a data repository and calculation means for the various data received from walker 10 while in use.

To adjust walker 10 to the proper height for an individual user, compression collars 24 are included on uprights 26a,b (FIG. 2) of each leg assemblies 12. Upright insert 28a,b telescopes in and out of upright 26a,b of leg assembly 12 so the overall length of leg assemblies 12 may be lengthened or shortened to accommodate a particular user. This is accomplished by releasing compression collars 24 and inserting or withdrawing upright insert 28a,b from upright 26a,b until the proper height of walker 10 is achieved. Compression collars 24 are then tightened to secure upright insert 28a,b at the desired length. While not shown, a similar type of adjustment method may be incorporated into lateral braces 16 in order to adjust the distance between leg assemblies 12 for the particular user. It will be appreciated by those skilled in the art that the distance between leg assemblies 12 must be sufficient to allow a user to comfortably ambulate with walker 10, and yet, sufficiently spaced in order that the application of the full weight of a user to one side or other of walker 10 will not cause the device to tip over.

Referring now to FIG. 2, handle assemblies 30 are mounted atop leg assemblies 12 and serve to isolate user forces and torques applied to walker 10. Handle assemblies 30 are connected to leg assemblies 12 by handle supports 20. Handle assemblies 30 are cantilevered from handle support 20 in order that determination of forces and torques applied to handle assemblies 30 are largely independent of leg assemblies 12 and the accuracy, precision, and sensitivity of the force and torque measuring devices are maintained at a high level.

Referring again to FIG. 2, it can be observed that leg assembly 12 is comprised of front upright 26a and rear upright 26b which are interconnected by cross braces 32 and diagonal brace 34. This square box-like configuration is utilized to provide maximum stability to walker 10 as patients of varying physical ability will put walker 10 to use. Those experienced in the art will recognize a number of variations in the general structure of walker 10 may be utilized such as an A-frame leg assembly having handle assemblies 30 mounted atop thereof. Any such convenient configuration of the structure of walker 10 may be utilized as long as the structure provides the user with dependable structural stability and a sufficiently light weight in order that elderly or physically limited users may conveniently ambulate with the walker.

Time and Distance Measurements

One parameter for measuring patient physical status and improvement during treatment of ambulation limiting injuries is measurement of distance traveled during ambulation and time required to achieve that distance. Measurement of this parameter is accomplished by incorporation of a distance measuring device within walker 10 such as distance gauge 18. It will be appreciated by those skilled in the art that depending upon the type of distance gauge 18 selected, the total elapsed time may be determined as well as the elapsed time for each interval of movement may be determined from such a device. In the present embodiment, distance gauge 18 is a wheel 14 attached to front uprights 26a of leg assemblies 12. In an alternative embodiment, distance gauge 18 may be on a central, additional leg spring-biased against the ground. In this manner the distance gauge maintains contact with the ground as a user lifts the walker.

In FIG. 5, wheel 14 is provided with incremental registrations 36a-c spaced at equal distances about the circumference of wheel 14. In the present embodiment, incremental registrations 36a-c are apertures through wheel 14. Attached to upright insert 28a is detector 38 through which wheel 14 and incremental registrations 36a-c pass. Detector 38 is equipped with light emitting diode (LED) 40 which causes light to pass through incremental registrations 36 as they pass through detector 38. This results in an intermittent flash of light on the opposite side of wheel 14 from LED 40 which is detected by a photoelectric cell (not shown) on the side of detector 38 opposite LED 40. The photoelectric cell provides a simple on-off response which is then recorded.

Typical output from the photoelectric cell is a square wave function, shown in Graph A, indicating the on-off response of the photoelectric cell. The detected responses can be correlated with the number of responses required to pass wheel 14 through its circumference, or a portion thereof, in order to calculate the distance traveled by a user of walker 10. Alternatively, a more sophisticated type of detector may be utilized which will permit tabulation of the passage of time between detection of each incremental registration 36 in order to provide the therapist or physician with timing information on each ambulation movement of a user utilizing walker 10.

Graph A
Output of distance guage

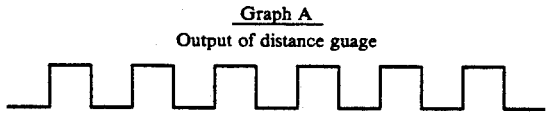

It will be appreciated by those skilled in the art that detector 38 could be in the form of a magnetic pickup in conjunction with a toothed gear mechanism or a simple revolution counter or a shaft encoder device in order to measure the rotation of wheel 14. Alternatively, a course of known distance could be utilized with a stop watch and the distance gauge function of walker 10 left to calculation by the therapist.

Referring again to FIG. 1, as data is collected by detector 38 it is passed to data console 22 through wire 42 passing in or along leg assembly 12. In this manner the therapist or physician can focus attention on the physical movements of the user of walker 10 and examine the collected data at the end of ambulation.

The data collected from distance gauge 18 can be utilized to determine a number of parameters regarding patient physical abilities including average distance traveled per step or stride length, and total ambulation speed. Increments of ambulation--relating a time to the performance of each of the various actions in ambulation--may also be determined. Measurements such as length of time and rate for shifting walker 10 forward can give an indication of upper body and back integrity. The time required for a user to then approach the newly positioned walker can give an indication of lower body ambulation abilities.

Determination of Load During Ambulation

The term "load" is taken to mean the application of force by a user on walker 10 as a result of reliance by the user on walker 10 to support a component of the user's weight. For purposes of this discussion, load refers, generally, to the vertical and lateral forces applied by a user to walker 10 as opposed to torque forces applied by a user to walker 10. Walker 10 and handle assembly 30 in a preferred embodiment are intended to withstand a maximum load of 280 pounds on each handle assembly 30. This corresponds to the nearly full weight of most users expected to be encountered.

The general principal of operation is that the detected output of the various sensors of walker 10 should be zero when no load or torque is applied to handle assemblies 30. As a user ambulates with walker 10, some amount of load and/or torque will be applied to handles 30 when the user relies upon walker 10 to support her weight and provide balance during ambulation. The load applied to handle assemblies 30 is detected as a strain in handle assemblies 30 as the material composing assemblies 30 responds to the applied load or force.

Referring now to FIG. 3, the sensors for detecting the response of handle assemblies 30 to the applied load are strain gauges or detectors 50a-d (FIGS. 3 and 4) which have been applied to strategic locations on handle assemblies 30 of walker 10. Referring now to FIG. 4, an enlarged view of a typical strain detector is presented. Strain detector 50a-d is of the resistance-type strain gauge and is adhesively bonded to locations on handle assemblies 30. As handle assemblies 30 receive a load, strain is developed within the material composing handle assemblies 30 which is transmitted to strain detector 50.

Resistance-type strain gauges, such as 50a-d, are well known and operate on the principal that the resistance of foil grid 52 (FIG. 4) changes in proportion to the load-induced strain on handle assemblies 30. The load induced strain produces expansions and/or contractions within foil grid 52 which results in a change in the electrical resistance of foil grid 52. This then is communicated to data console 22 of walker 10 by leads 54 attached to foil grid 52. Foil grid 52 is a metal bonded to a thin plastic film 56 which serves as a backing or carrier for grid 52. Carrier film 56 also serves as electrical insulation between grid 52 and handle assemblies 30. The selection of the particular strain gauge 50 to be utilized and the proper attachment of the gauge to walker 10 may be determined from the available texts on strain gauge applications.

In use on the present embodiment, strain gauges 50a-d are placed in four different locations on handle assemblies 30 in order to provide detection of strain.

The detected strain is then compared against an unstrained gauge to provide for temperature correction.

Referring now to FIG. 3, gauge 50a is placed on a portion of handle assembly 30 that is not subject to loading by a user. Gauge 50a is not subject to changes in resistance due to distortion of its grid 52 from load or torque, but will exhibit changes in resistance due to changes in temperature. Therefore, changes in resistance in gauge 50a may be determined and utilized to correct for temperature changes in the load-detecting strain gauge to eliminate an error. It will be observed that the longitudinal axis of strain gauge or sensor 50a is perpendicular to the longitudinal axis of handle assembly 30. This perpendicular placement assists in limiting any effects of strain which might be transmitted through handle support 20 and affect gauge 50a.

Sensor or strain gauge 50c is positioned on the inward vertical surface of arm 31 of handle assembly 30. Strain gauge 50c is so positioned in order to measure inward and outward directed forces applied to arm 31 by a user. The longitudinal axis of strain gauge 50c is oriented parallel to the longitudinal axis of arm 31 in order to maximize sensitivity to the applied load.

Detectors 50d are placed on the underside of arms 31 with the longitudinal axis of the detector aligned with the longitudinal axis of arm 31. Detector 50d is positioned in order to efficiently measure upward and downward forces applied to arms 31. When a user is utilizing walker 10, the largest component of force or load on walker 10 will be the downward load measured by sensor 50d, and alternately the upward force as the user lifts walker 10 in order to move it forward in preparation for taking another step.

It will be appreciated by those skilled in the art that the signal of gauge 50c,d may be detected by interconnection of detectors 50a-d in suitable pairings within a Wheatstone bridge. For example, in the present embodiment temperature detector or dummy detector 50b is connected in conjunction with downward force detector 50d within the conventional circuit arrangement known as the Wheatstone bridge. In this connection the signal from dummy detector 50b cancels out the signal from active detector 50d to produce a signal of zero millivolts when walker 10 is resting and without any load placed upon arm 31. When a load is applied to arm 31 and the arm is forced downward by the weight of a user the resistance wire in detector 50d becomes compressed. This changes the resistance of detector 50d. The difference in output of detector 50d, as compared to dummy detector 50b within the bridge, is transmitted to data console 22 where the bridge output in millivolts is amplified to volts for easier detection by recording devices.

A similar Wheatstone bridge is utilized in connecting temperature or dummy connector 50a with lateral strain sensor or gauge 50c. Once again, the Wheatstone bridge is utilized to provide zero response when walker 10 is not in use and to provide detection of the force applied in an outward or inward manner to arm 31 by a user.

The output from the detectors can be expected to be linear throughout the detection range. In order to associate a particular voltage output with an applied load or force, a simple calibration graph can be developed such as in Graph B. In less sophisticated devices the force applied to each handle assembly 30 may be read from the graph. In more sophisticated devices, the slope of the line plotted in the calibration graph may be utilized to directly calculate the force from the detected voltage.

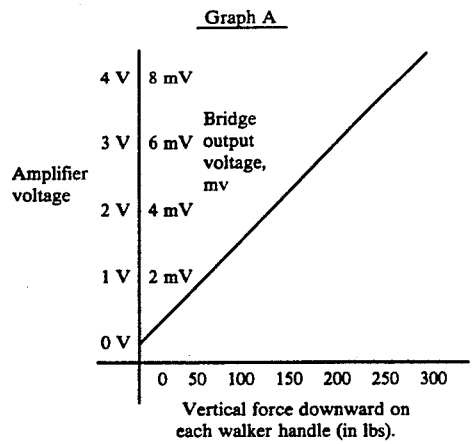

Graph A

Detection of Torque

Also mounted on handle assembly 30, specifically on arm 31, is a fifth array of resistance-wire sensors or detectors 60. Torque measurement array 60 is comprised of four resistance-wire strain gauges mounted on opposed sides of arm 31. As shown in FIG. 6 and FIG. 3, torque strain gauges 60a, 60c are mounted on the upper side of arm 31 and strain gauges 60b and 60d are mounted on the lower side of arm 31. Strain gauges 60a-d are connected in a Wheatstone bridge. Gauges 60a and 60d are mounted on a line forming a right-handed helix 62 about arm 31 to sense a positive strain on arm 31, and gauges 60c and 60b mounted along a line forming a left-handed helix 63 to sense negative strain in arm 31. The two 45° helixes 62, 63 define the principal stress and strain directions for arm 31 subject to torsion by a user of walker 10.

Method of Operation

The method associated with the apparatus comprises selecting a user for physical ability analysis and instructing him to use walker 10 in the fashion of a normal walker. This involves the patient setting walker 10 in a position forward of his body and then utilizing walker 10, to whatever extent necessary, to support the user's weight as he approaches the newly positioned walker. This results in a force or load and torque being placed upon arms 31 of handle assemblies 30 causing an expansion or contraction of the resistance-wire strain gauges mounted on handle assembly 30 in turn causing a change in the voltage output from the Wheatstone bridge which is directly proportional to the force or torque placed upon handle assembly 30 by the user. The voltage output is then communicated to data console 22 for analysis.

The analysis performed on the collected data consists of examining the detected force and torque components applied to handle assembly 30 and correlating these components of force and torque with the time and distance measurements accrued during the patient ambulation. This permits the therapist or physician to determine the rapidity with which each movement is made and the degree of reliance by the patient on the walker. The various detected force components may also be compared on a day-to-day or week-to-week basis in order to evaluate patient improvement during a course of therapy or during healing.

This comparative data evaluation over weeks or months permits objective analysis of the benefit of the applied therapy. Also more objective decisions related to whether therapy should be discontinued or an alternate therapy employed can be made.

It is to be understood that while certain forms of this invention have been illustrated and described, it is not limited thereto except insofar as such limitations are included in the following claims and allowable functional equivalents thereof.

We claim:

1. An apparatus for determining the ambulation capacity of a user comprising:
   a user moveable frame for supporting the user during ambulation, said frame being moveable by the user to support the user in ambulation,
   handle means on said frame for receiving the force of the weight of an ambulating user,
   means for measuring the force thereon as user body weight is supported by said frame during ambulation, and
   means for determining the distance said frame is moved by a user during ambulation.

2. The apparatus as claimed in claim 1, wherein said means for measuring downward force is a strain gauge coupled to said handle.

3. The apparatus as claimed in claim 1, further comprising means for measuring torque applied thereto by a user during ambulation.

4. The apparatus as claimed in claim 3, wherein said means for measuring torque is a strain gauge adapted to measuring torque applied to said handle.

5. The apparatus as claimed in claim 1, wherein said means for determining distance comprises: a wheel attached to the base of said frame for contact with a floor, and a counter for measuring the amount of rotation of said wheel during ambulation.

6. The apparatus as claimed in claim 1, further comprising timer means for measuring the elapsed time during said user ambulation.

7. An apparatus for determining the ambulation abilities of a user comprising:
   a frame moveable by a user while supporting the user during ambulation,
   handle means on said frame for gripping by the user and to receive the force from supporting a portion of the user's weight during user ambulation, and
   means for measuring strain on said frame from supporting said user weight.

8. The apparatus as claimed in claim 7, wherein said means for measuring strain is a strain gauge coupled to said handle.

9. The apparatus as claimed in claim 7, wherein said means for measuring strain comprises a torque strain gauge coupled to said handle.

10. The apparatus as claimed in claim 7, further comprising means for determining the distance said frame is moved by a user during ambulation.

11. The apparatus as claimed in claim 10, wherein said means for determining distance comprises: a wheel attached to the base of said frame for contact with a floor, and a counter for measuring the amount of rotation of said wheel during ambulation.

12. The apparatus as claimed in claim 7, further comprising timer means for measuring the elapsed time during said user ambulation.

13. A method for determining the ambulation abilities of a user comprising:
    providing a user with an apparatus, said apparatus being moveable by the user while supporting a component of the user's weight thereon during ambulation,
    equipping said apparatus with means for measuring the forces applied to said apparatus from supporting said user weight,
    measuring the forces applied to said apparatus during user ambulation, and
    evaluating the detected forces to determine patient physical status.

14. The method as claimed in claim 13, wherein said means for measuring force comprises resistance-wire strain gauges mounted on said apparatus to detect the force applied to said apparatus from supporting said user weight as strain on said apparatus.

15. The method as claimed in claim 13, further comprising the step of determining the distance said apparatus is moved by a user during ambulation.

16. The method as claimed in claim 13, further comprising the step of measuring the elapsed time during said user ambulation.

17. The method as claimed in claim 13, wherein said evaluating step comprises:
    measuring the forces applied to said apparatus during a user ambulation first time period,
    measuring the forces applied to said apparatus during a user ambulation time period after said first time period, and
    comparing said force measurements of said first time period with said second time period to determine user improvement in ambulation.

18. The method as claimed in claim 17, wherein said means for measuring force comprises a resistance-wire strain gauge mounted on said apparatus to detect the force applied to said apparatus from supporting said user weight as strain on said apparatus.

19. The method as claimed in claim 13, wherein said means for measuring force comprises spring force detection gauge mounted on said apparatus to detect the force applied to said apparatus from supporting said user weight on said apparatus.

* * * * *